United States Patent [19]
Chelnokov et al.

[11] 4,024,860
[45] May 24, 1977

[54] APPARATUS FOR DRAWING TOGETHER AND FIXING THE PELVIC HALVES IN PUBIC SYMPHYSIS RUPTURES

[76] Inventors: Gennady Ivanovich Chelnokov, ulitsa Scherbakova, 13, kv. 51, Mytischi Moskovskoi oblasti; Leonid Gershevich Ruvinsky, ulitsa Akademika Komarova, 6, kv. 30, Moscow; Igor Leonidovich Kovalenko, ulitsa Chapaeva, 7, kv. 30, Khimki Moskovskoi oblasti; Ivan Ivanovich Sokolov, ulitsa V. Ulbrikhta, 19/10, kv. 55, Moscow; Nikolai Semenovich Belyaev, ulitsa B. Rupasovskaya, 35, Mytischi Moskovskoi oblasti; Vladimir Pavlovich Okhotsky, ulitsa V. Ulbrikhta, 4, korpus 2, kv. 69; Leonid Lavrentievich Belyshev, ulitsa Akademika Komarova, 13, kv. 52, both of Moscow, all of U.S.S.R.

[22] Filed: Jan. 5, 1976

[21] Appl. No.: 646,489

[52] U.S. Cl. .............................. 128/84 R; 128/92 A
[51] Int. Cl.² ........................................... A61F 5/04
[58] Field of Search ............. 128/92 A, 92 R, 92 G, 128/84 R, 84 C, 83

[56] References Cited
OTHER PUBLICATIONS

Brendel's Symphysis Reduction Tractor, Surgery, Gynecology, & Obstetrics, July 1945, p. 60.

*Primary Examiner*—John D. Yasko
*Attorney, Agent, or Firm*—Steinberg & Blake

[57] ABSTRACT

The proposed apparatus for drawing together and fixing the pelvic halves on pubic symphysis ruptures comprises a U-shaped frame whereof the ends carry elastic members designated to cooperate with the patient's body. The elastic members are rotatably mounted and adapted to move toward each other. The elastic members are moved toward each other and caused to exert a required compressive force on the patient's body by means of servos coupled to a power source.

7 Claims, 5 Drawing Figures

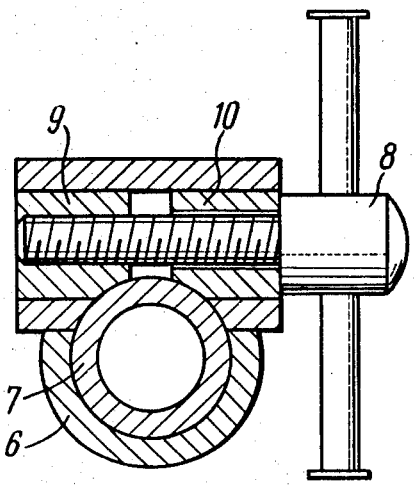
FIG. 2
FIG. 3
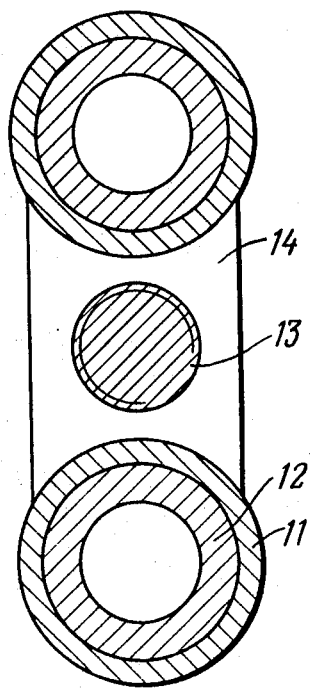

APPARATUS FOR DRAWING TOGETHER AND FIXING THE PELVIC HALVES IN PUBIC SYMPHYSIS RUPTURES

The present invention relates to medical equipment and, more particularly, to devices employed in traumatology; it is directed to apparatus for drawing together and fixing the pelvic halves in pubic symphysis ruptures.

The apparatus of the present invention may find application during surgical or medicamentous treatment of the pubic symphysis, in the course of surgery for inveterate traumas as well as in obstetrics for preventing pubic symphysis ruptures.

The most wide-spread procedures for drawing together and fixing the pelvic bones currently in use in the art are bandaging of the pelvis and application of plaster casts. To this end, use is made e.g. of a linen belt crossing in front, Gilferding's cloth belt, Percy's leather belt, M. A. Dubinina's bandage, Conwell's bandage, or N. N. Yelanski's plaster cast.

It is likewise known in the art to employ Juss' apparatus for drawing together and fixing the pelvic halves, which is formed as a plaster cast applied to the patient's body from the inguinal folds as far as the toes. Metal sleeves with screws are built into the cast at the level of the upper third of the thigh and at the level of the ankles, making it possible to draw together the limbs and the pelvic halves.

However, all the above known devices are applied to the patient's body for a prolonged period of time and bring constant pressure to bear on the soft tissues, causing circulation disturbances at the sites of cast application which result in necrosis and bedsores. Furthermore, the prior art devices are cumbersome and difficult to handle, interfering with the nurse's duties. Besides, these devices are of little use as far as inveterate fractures are concerned, for they fail to provide the requisite compressive effort at a given point in time.

It is further known in the art to employ Hoffmann's apparatus which uses screw shafts attached to the iliac crests with the aid of wood screws, whereby the pubic bones are brought together. The disadvantage of this latter apparatus consists in that the wood screws which are fixed in the iliac crests fail to withstand the considerable loads associated with the treatment of inveterate ruptures of the pubic symphysis.

It is an object of the present invention to provide an apparatus for drawing together and fixing the pelvic halves in pubic symphysis ruptures, which would enable the pelvic girdle to be repositioned and fixed by means of a widely adjustable directed force applied externally to the pelvic bones, the entire procedure being relatively effortless for the surgeon.

It is another object of the present invention to provide an apparatus which would ensure a constant level of pressure on the patient's body at shifting points of application, thereby obviating any possibility of soft tissue necrosis in the course of treatment.

The foregoing object are attained by the provision of an apparatus for drawing together and fixing the pelvic halves in pubic symphysis ruptures, which, in accordance with the invention, comprises a U-shaped frame mounted on supports, two elastic members designed to cooperate with the patient's body which are mounted on the ends of said frame so as to be able to move toward each other and rotate about an axis parallel to the direction of the countermovement, servos connected with the elastic members which provide for said counter motion thereof and cause the elastic members to press against the patient's body with a required force for a required length of time, and a power source coupled to the servos.

The elastic members may be attached to the frame with the aid of a plurality of sleeves disposed coaxially a certain distance one from another and able to execute a limited longitudinal motion one with respect to another, and a cylindrical hinge disposed in coaxial relationship with said sleeves, and the servos may be formed as bellows disposed inside the sleeves, said bellows being fastened at one end to the elastic members and coupled at the other end to the frame by way of said cylindrical hinge. Thus, when the elastic members are pressed against the patient's body, they are capable thereby of aligning themselves at an angle to the side arms of the frame, making for a more secure fit to the patient's body.

The crossarm and the side arms of the V-shaped frame are preferably formed as extensible elements.

The elastic members should desirably have a plurality of inner chambers alternately interconnected into several groups which are by turns coupled to a compressed air source. Such an arrangement provides for a normal blood supply to the soft tissues in the course of prolonged treatment without interfering with the constancy of the compressive force, thereby allowing soft tissue necrosis to be avoided.

The drawing together and fixing of the pelvic bones in the proposed apparatus requires no physical effort on the part of the surgeon, being effected by means of a directed force externally applied to the pelvic girdle.

The proposed apparatus enables the pelvic bones to be drawn together and fixed in a desired position, which makes it a valuable aid to the surgeon.

The proposed apparatus effectively transmits all effort to the pelvic bones and is simple to maintain and adjust.

The invention will be further understood from the following description of an exemplary embodiment thereof taken in conjunction with the accompanying drawings, wherein:

FIG. 2 is a blown-up sectional view taken on the line II—II in FIG. 1;

FIG. 3 is a blown-up sectional view taken on the line III—III in FIG. 1;

Figure 1:
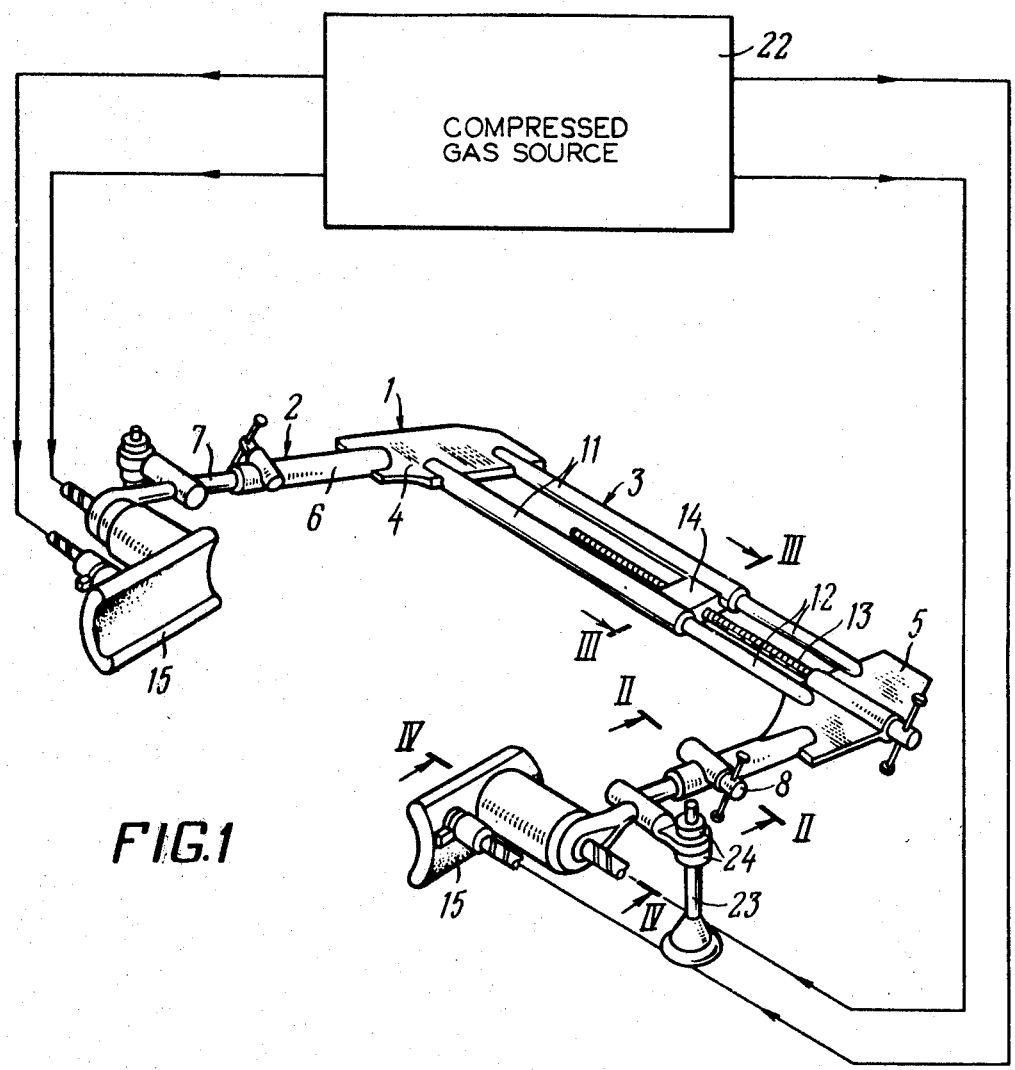
FIG. 1 is a general view of an apparatus for drawing together and fixing the pelvic halves in pubic symphysis ruptures, in accordance with the invention.

Referring now to the drawings, the proposed apparatus for drawing together and fixing the pelvic halves in pubic symphysis ruptures comprises a U-shaped frame 1 (FIG. 1) having side arms 2 and a crossarm 3 which are fastened together by plates 4 and 5 imparting additional rigidity to the structure. The side arms 2 of the frame 1 are telescopic in design, comprising sleeves 6 accommodating rods 7 capable of moving along the sleeves 6 and turning therein. The rods 7 are locked in the sleeves 6 with the aid of a screw 8 acting on sleeves 9 and 10 (FIG. 2).

The crossarm 3 (FIG. 1) is likewise an extensible member comprising two guide sleeves 11 (FIGS. 1 and 3) rigidly connected with the plate 4, rods 12 rigidly connected with the plate 5 fitting into the guide sleeves 11. The rods 12 are moved along the sleeves 11 by means of a screw 13 which cooperates with a threaded hole in a tie piece 14 rigidly connecting the two sleeves 11 (FIG. 3).

Attached to the ends of the frame 1 (FIG. 1), viz. of the side arms 2 thereof, are two elastic members 15 designed to cooperate with the patient's body. In order that the elastic members 15 may move toward each other, they are secured to the frame 1 by means of telescopic sleeves 16, 17 and 18 (FIG. 4) disposed coaxially a certain distance one from another and capable of executing a limited longitudinal motion one with respect to another. The outer sleeve 18 is attached to the elastic member 15, while the inner sleeve 16 is connected with the side arm 2 by way of a cylindrical hinge 19 coaxial with respect to the sleeves 16, 17 and 18.

The sleeve 16 accomodates a bellows 20 functioning as a servo. At one end the bellows 20 is attached to the elastic member 15, while at the other end it is connected with the side arm 2 by way of the hinge 19. The bellows is provided with guard rings 21 delimiting the minimal height of the bellows 20.

The servo may likewise be constituted by any of various known hydraulic, pneumatic or mechanical driving mechanisms.

The bellows 20 are coupled to a pressure source 22 (FIG. 1) which may be formed by any of various devices whereby excess pressure can be generated, such as compressed gas cylinders or various compressors and pumps.

With the elastic members 15 being attached to the side arms 2 by means of the telescopic sleeves 16, 17 and 18 (FIG. 4), which are disposed a certain distance one from another, and with the bellows 20 being employed as the servo, the elastic members 15 are able to change somewhat their angular position with respect to the side arms 2, seeking a better fit to the patient's body owing to the cylindrical hinge 19. The elastic members 15 are further able to rotate about axes parallel to the direction of their counter motion. The elastic members 15 likewise turn as the rods 7 (FIG. 1) turn inside the sleeves 6.

Besides, the above-described design of the frame 1 with its extensible side arms 2 and cross arm 3 also enables the spatial position of the elastic members 15 to be altered. The frame 1 is mounted on a table (not shown) on supports 23 whereof the height is adjusted with the aid of nuts 24.

In order that the patient's soft tissues at the points of application of the compressive force may avoid damage, the elastic members 15 are provided with a plurality of alternately interconnected inner chambers whereby the points of application of the compressive force can be shifted. In the particular exemplary embodiment described herein, all inner chambers make up two groups: one group is constituted by interconnected inner chambers 25 (FIGS. 4 and 5) while the other by inner chambers 26, the chambers 25 and 26 alternating.

Figure 4:
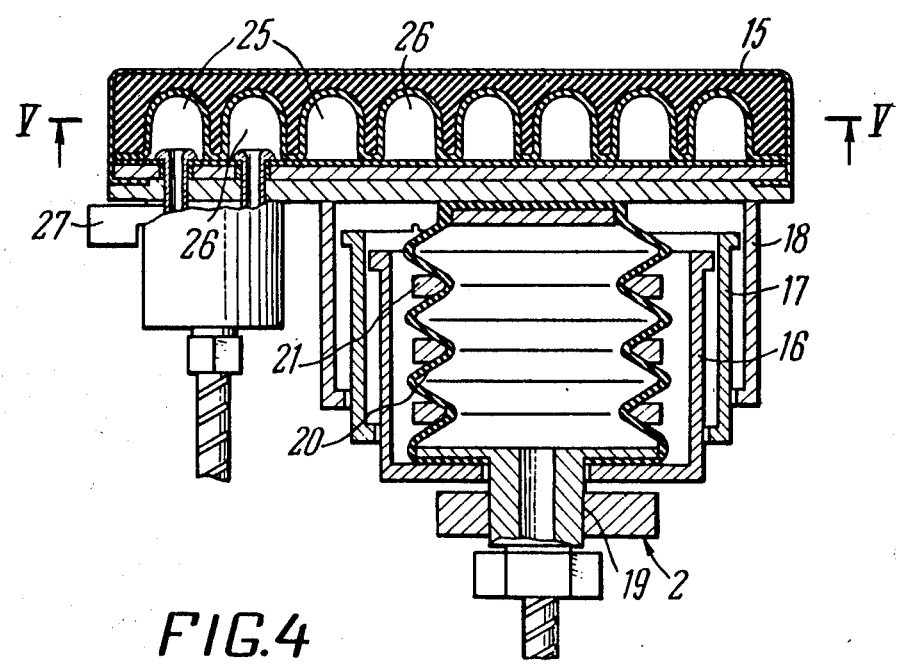
FIG. 4 is a blown-up sectional view taken on the line IV—IV in FIG. 1.
Figure 5:
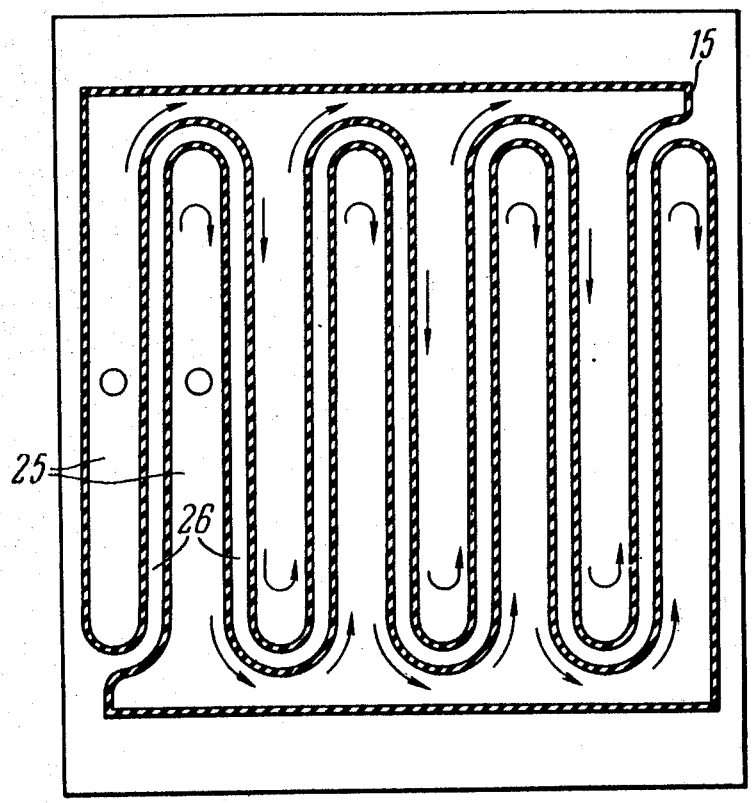
FIG. 5 is a sectional view taken on the line V—V in FIG. 4.

However, the number of groups of inner chambers may be more than two, and the inner chambers making up such groups may be variously arranged, e.g. in a staggered order, with respect to the surfaces of the elastic members 15 which adjoin the patient's body. Each group of chambers is connected to a pressure source so that compressed air is supplied by turns now into the group of chambers 25 now into the chambers 26. The source of pressure may be constituted by that same source 22 (FIG. 1) which communicates with the bellows 20 (FIG. 4). The alternate air supply into the two groups of chambers 25 and 26 from the source 22 (FIG. 1) is effected with the aid of a cock 27 (FIG. 4) which may be constituted e.g. by a slide valve.

The proposed apparatus for drawing together and fixing the pelvic halves in pubic symphysis ruptures operates in the following manner.

The patient is positioned on the table so that the elastic members 15 are aligned with the pelvic halves and the cross arm 3 (FIG. 1) of the frame 1 is under the legs. Then, moving the nuts 24 along the supports 23, the height adjustment of the elastic members 15 is carried out. If need be, the position of the elastic members 15 is further adjusted by turning same in the hinges 19 (FIG. 4) as well as by turning the rods 7 (FIG. 1) in the sleeves 6 or by extending the side arms 2, locking same in a required position by means of the screw 8. At the preliminary stage, the pelvic halves are drawn together and fixed by turning the screw 13 whereby the cross arm 3 is shortened, the elastic members 15 squeezing the pelvic halves with a specified force and fixing them.

The compressive and fixing effort is adjusted and the elastic members 15 are caused to additionally move toward each other and exert a desired compressive effort on the patient's body for a specified time by supplying specified quantities of compressed air into the bellows 20 (FIG. 4) from the pressure source (FIG. 1). To prevent necrosis of the soft tissues in the course of treatment, the points of application of the compressive and fixing force are shifted by alternately supplying compressed air now to the group of chambers 25 (FIG. 4) now to the group of chambers 26 of the elastic members 15, which is done with the aid of cock 27 (FIG. 4).

What is claimed is:

1. An apparatus for drawing together and fixing the pelvic halves in pubic symphysis ruptures, which comprises: a U-shaped frame; supports whereon said frame is mounted; two elastic members designed to cooperate with the patient's body which are disposed on the ends of said frame and are adapted to move toward each other as well as turn about an axis parallel to the direction of said counter motion; servos coupled to said elastic members which provide for said counter motion of said elastic members and cause the latter to exert a desired compressive effort on the patient's body for a specified length of time; and a power source coupled to said servos.

2. An apparatus as set forth in claim 1, which comprises: a plurality of sleeves disposed coaxially a certain distance one from another and capable of executing a limited longitudinal motion one with respect to another, the outer sleeve being fastened to said elastic member; a bellows serving as said servo which is disposed inside the inner one of said sleeves and attached at one end to said elastic member; and a cylindrical hinge coaxial with respect to said sleeves which connects the other end of said bellows and said inner sleeve with said frame.

3. An apparatus as set forth in claim 1, wherein said U-shaped frame is composed of side arms constructed as extensible members and a cross arm likewise constructed as an extensible member.

4. An apparatus as set forth in claim 2, wherein said U-shaped frame is composed of side arms constructed as extensible members and a cross arm likewise constructed as an extensible member.

5. An apparatus as set forth in claim 1, which comprises: inner chambers formed in said elastic members and alternately interconnected to form several groups; and a pressure source for alternately supplying compressed air to said groups of said chambers.

6. An apparatus as set forth in claim 2, which comprises: inner chambers formed in said elastic members and alternately interconnected to form several groups; and a pressure source for alternately supplying compressed air into said groups of said chambers.

7. An apparatus as set forth in claim 3, which comprises: inner chambers formed in said elastic members and alternately interconnected to form several groups; and a pressure source for alternately supplying compressed air into said groups of said chambers.

* * * * *